US012558057B2

(12) United States Patent
Tao et al.

(10) Patent No.: US 12,558,057 B2
(45) Date of Patent: Feb. 24, 2026

(54) ULTRASONIC IMAGING METHOD, ULTRASONIC IMAGING SYSTEM, AND NON-TRANSITORY COMPUTER-READABLE MEDIUM

(71) Applicant: GE Precision Healthcare LLC, Waukesha, WI (US)

(72) Inventors: Ke Tao, Wuxi (CN); Minyu Gu, Wuxi (CN); Zhiwen Wang, Wuxi (CN); Gang Liu, Wuxi (CN); Shangjie Du, Wuxi (CN); Junjun Chen, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/619,848

(22) Filed: Mar. 28, 2024

(65) Prior Publication Data

US 2024/0324984 A1      Oct. 3, 2024

(30) Foreign Application Priority Data

Mar. 31, 2023    (CN) .......................... 202310341889.9

(51) Int. Cl.
| | |
|---|---|
| *A61B 8/00* | (2006.01) |
| *A61B 8/08* | (2006.01) |
| *A61B 17/34* | (2006.01) |

(52) U.S. Cl.
CPC .......... *A61B 8/0841* (2013.01); *A61B 8/4209* (2013.01); *A61B 8/461* (2013.01); *A61B 8/54* (2013.01); *A61B 17/3403* (2013.01); *A61B 2017/3409* (2013.01); *A61B 2017/3411* (2013.01)

(58) Field of Classification Search
CPC ..... A61B 8/0841; A61B 8/4209; A61B 8/461; A61B 8/54; A61B 17/3403; A61B 2017/3409; A61B 2017/3411; A61B 8/085; A61B 2017/3413; A61B 34/20; A61B 8/44; A61B 8/469; A61B 2034/2063
See application file for complete search history.

(56) References Cited

U.S. PATENT DOCUMENTS

2007/0043291 A1*    2/2007   Fidel ................... A61B 8/4281
                                                          600/439

FOREIGN PATENT DOCUMENTS

| | | | |
|---|---|---|---|
| CN | 114271908 A | 4/2022 | |
| CN | 113349897 B | 3/2023 | |
| WO | WO-2016135595 A1 * | 9/2016 | ....... A61B 17/00234 |

* cited by examiner

*Primary Examiner* — Michael J Carey
*Assistant Examiner* — Zainab Mohammed Aldarraji

(57)    ABSTRACT

An interventional procedure performed on a structure of interest by using a grid assembly to guide an interventional object includes: acquiring a coordinate point set of a position to be subjected to intervention on an ultrasound image of the structure of interest; and controlling, on the basis of the coordinate point set, a display unit on the grid assembly to cause the display unit to generate a first visual indication for an interventional hole which is on the grid assembly and which falls within the coordinate point set.

14 Claims, 6 Drawing Sheets

100

100

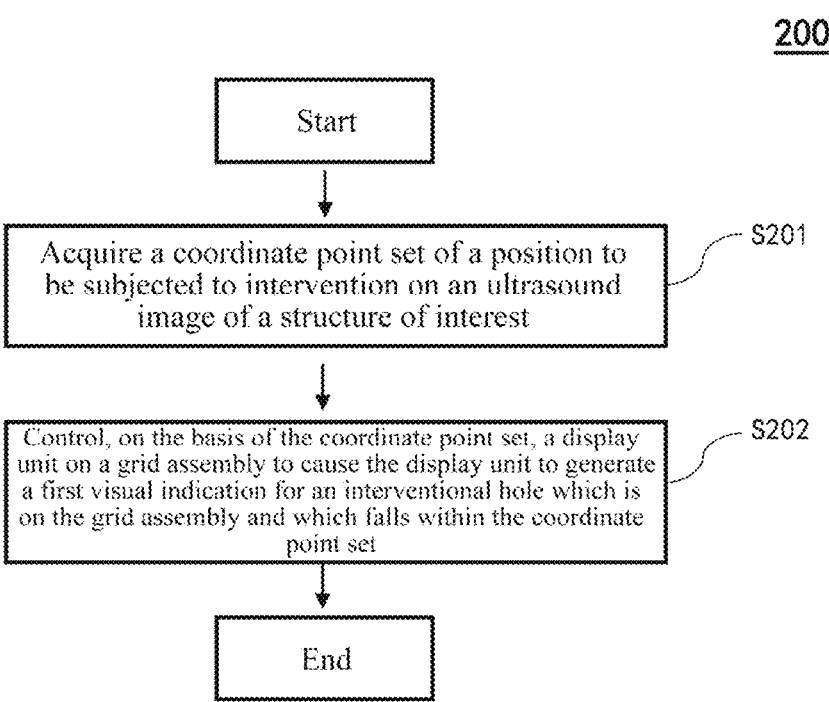

200

Start

Acquire a coordinate point set of a position to be subjected to intervention on an ultrasound image of a structure of interest ⟋ S201

Control, on the basis of the coordinate point set, a display unit on a grid assembly to cause the display unit to generate a first visual indication for an interventional hole which is on the grid assembly and which falls within the coordinate point set ⟋ S202

End

FIG. 2

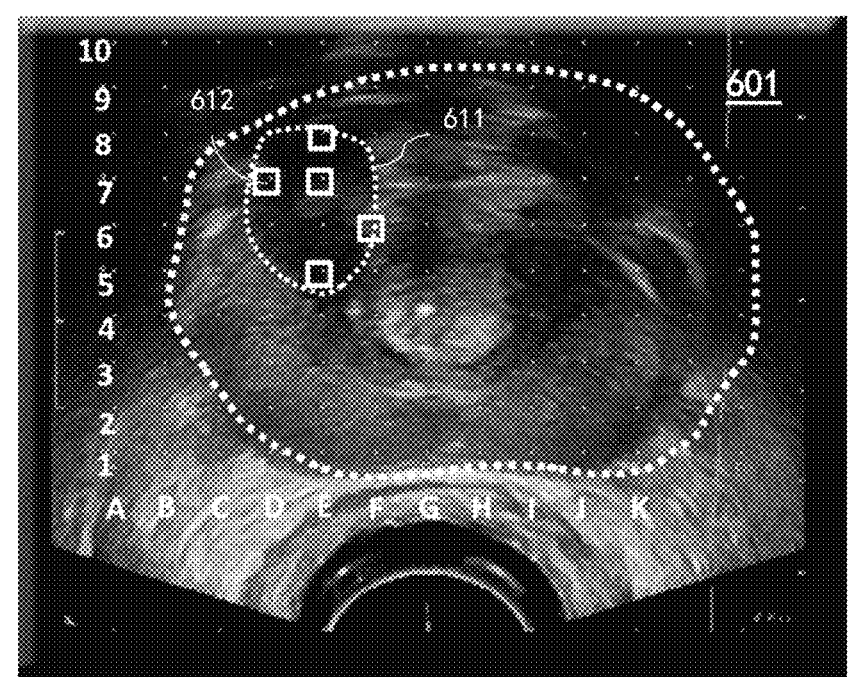
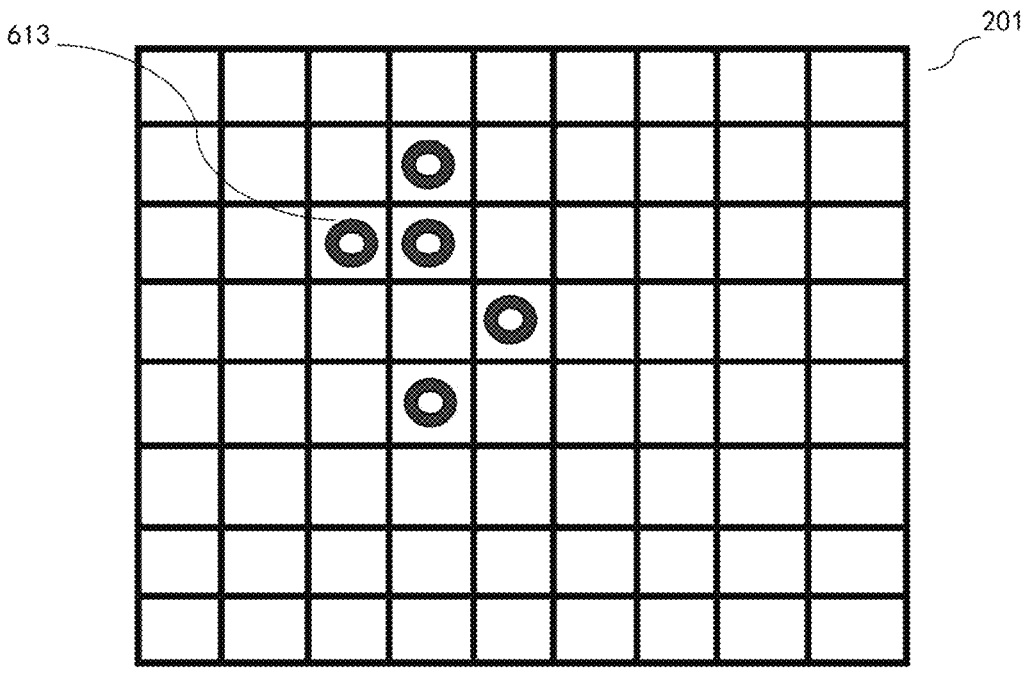
FIG. 6

ULTRASONIC IMAGING METHOD, ULTRASONIC IMAGING SYSTEM, AND NON-TRANSITORY COMPUTER-READABLE MEDIUM

CROSS-REFERENCE TO RELATED APPLICATION

The present application claims priority to Chinese Patent Application No. 202310341889.9, filed on Mar. 31, 2023. The entire contents of the above-listed application are incorporated by reference herein in their entirety.

TECHNICAL FIELD

The present invention relates to the field of ultrasonic imaging and, in particular, to an ultrasonic imaging method, an ultrasonic imaging system, and a non-transitory computer-readable medium.

BACKGROUND

Ultrasonic imaging technology is a real-time, lossless imaging technology that utilizes a probe to receive an ultrasonic echo signal from a site to be imaged, and then processes the ultrasonic echo signal to perform imaging. In some application scenarios, ultrasonic imaging can assist, in real time, in the determination of the position of a structure of interest (e.g., a lesion) in an interventional operation (e.g., a biopsy or treatment). For example, in an interventional operation of the prostate, a doctor may use a probe running through a cavity (e.g., the rectum) to image the prostate and a lesion in the prostate in real time, so as to assist the doctor in determining the position of the lesion, so as to accurately perform sampling and/or treatment.

When an interventional operation is performed by using an interventional object (e.g., a needle), a grid plate is typically used. The grid plate includes a plurality of interventional holes. Position coordinates of these interventional holes may correspond to coordinates on an ultrasound image generated by an ultrasonic imaging system. In this way, an operator can determine, by observing a structure of interest on the ultrasound image, a coordinate point set on which an interventional operation needs to be performed, and then find a corresponding coordinate point (i.e., an interventional hole) set from upon the grid plate to perform a next operation. In the above-described process, the line of sight of the operator needs to continually switch between the ultrasound image and the grid plate, and whether a coordinate point selected on the grid plate is correct continually needs to be determined, thus causing the process of the operation to be time consuming and laborious.

SUMMARY

The aforementioned defects, deficiencies, and problems are solved herein, and these problems and solutions will be understood through reading and understanding the following description.

Provided in some embodiments of the present application is an ultrasonic imaging method. An interventional procedure is performed on a structure of interest by using a grid assembly to guide an interventional object. The method comprises: acquiring a coordinate point set of a position to be subjected to intervention on an ultrasound image of the structure of interest; and controlling, on the basis of the coordinate point set, a display unit on the grid assembly to cause the display unit to generate a first visual indication for an interventional hole which is on the grid assembly and which falls within the coordinate point set.

Provided in some embodiments of the present application is an ultrasonic imaging system, comprising: a probe, comprising an ultrasonic transducer; a processor, configured to: acquire a coordinate point set of a position to be subjected to intervention on an ultrasound image of a structure of interest, and control, on the basis of the coordinate point set, a display unit on a grid assembly to cause the display unit to generate a first visual indication for an interventional hole which is on the grid assembly and which falls within the coordinate point set; a display device, configured to receive a signal from the processor and perform display; and the grid assembly, which communicates with the processor.

Provided in some embodiments of the present application is a non-transitory computer-readable medium, having a computer program stored therein, the computer program having at least one code segment, and the at least one code segment being executable by a machine to perform the following method steps: acquiring a coordinate point set of a position to be subjected to intervention on an ultrasound image of a structure of interest; and controlling, on the basis of the coordinate point set, a display unit on a grid assembly to cause the display unit to generate a first visual indication for an interventional hole which is on the grid assembly and which falls within the coordinate point set.

It should be understood that the brief description above is provided to introduce, in a simplified form, concepts that will be further described in the detailed description. The brief description above is not meant to identify key or essential features of the claimed subject matter. The scope is defined uniquely by the claims that follow the detailed description. Furthermore, the claimed subject matter is not limited to implementations that solve any deficiencies raised above or in any section of the present disclosure.

BRIEF DESCRIPTION OF THE DRAWINGS

The present application will be better understood by reading the following description of non-limiting embodiments with reference to the accompanying drawings, wherein:

FIG. 2 is a schematic diagram of an ultrasonic imaging method according to some embodiments of the present application;

FIG. 6 is a schematic diagram of controlling display of a grid assembly according to some embodiments of the present application.

DETAILED DESCRIPTION

Specific embodiments of the present invention will be described in the following. It should be noted that in the specific description of the embodiments, it is impossible to describe all features of the actual embodiments of the present invention in detail, for the sake of brief description. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and tedious, for a person of ordinary skill in the art related to the content disclosed in the present invention, some design, manufacture, or production changes made on the basis of the technical content disclosed in the present disclosure are only common technical means, and should not be construed as the content of the present disclosure being insufficient.

Unless otherwise defined, the technical or scientific terms used in the claims and the description should be as they are usually understood by those possessing ordinary skill in the technical field to which they belong. "First", "second", and similar words used in the present invention and the claims do not denote any order, quantity, or importance, but are merely intended to distinguish between different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

Figure 1:
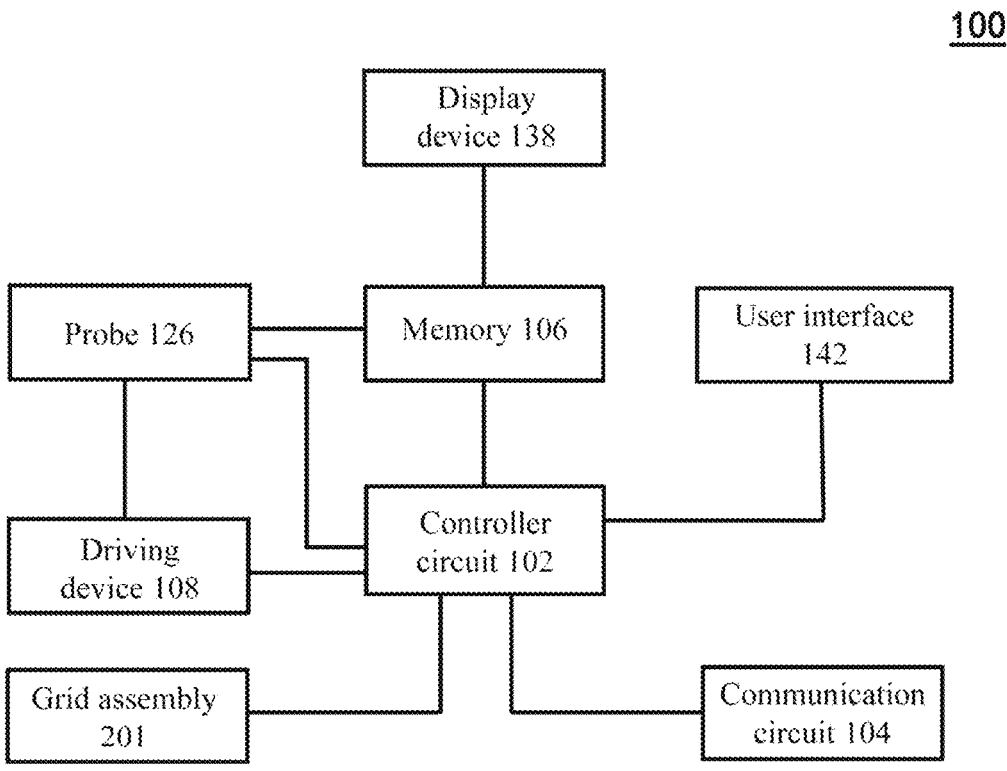
FIG. 1 is a schematic diagram of an ultrasonic imaging system according to some embodiments of the present application.

FIG. 1 shows a schematic block diagram of an embodiment of an ultrasonic imaging system 100. The ultrasonic imaging system 100 may include a controller circuit 102 operatively connected to a communication circuit 104, a display device 138, a user interface 142, a probe 126, a driving device 108, a grid assembly 201, and a memory 106.

The controller circuit 102 is configured to control operations of the ultrasonic imaging system 100. The controller circuit 102 may include one or more processors. Optionally, the controller circuit 102 may include a central processing unit (CPU), one or more microprocessors, a graphics processing unit (GPU), or any other electronic assembly capable of processing inputted data according to a specific logic instruction. Optionally, the controller circuit 102 may include and/or represent one or more hardware circuits or circuitry, the hardware circuits or circuitry including, connecting, or including and connecting one or more processors, controllers, and/or other hardware logic-based devices. Additionally or alternatively, the controller circuit 102 may execute an instruction stored on a tangible and non-transitory computer-readable medium (e.g., the memory 106).

The controller circuit 102 may be operatively connected to and/or control the communication circuit 104. The communication circuit 104 is configured to receive and/or transmit information along a bidirectional communication link with one or more alternate ultrasonic imaging systems, remote servers, etc. The remote server may represent and include patient information, a machine learning algorithm, a remotely stored medical image from a previous scan, and/or a diagnosis and treatment period of a patient, etc. The communication circuit 104 may represent hardware for transmitting and/or receiving data along a bidirectional communication link. The communication circuit 104 may include a transceiver, a receiver, a transceiver, etc., and associated circuitry (e.g., an antenna) for communicating (e.g., transmitting and/or receiving) with the one or more alternate ultrasonic imaging systems, remote servers, etc., by using a wired and/or wireless means. For example, protocol firmware for transmitting and/or receiving data along a bidirectional communication link may be stored in the memory 106 accessed by the controller circuit 102. The protocol firmware provides network protocol syntax to the controller circuit 102 so as to assemble a data packet, establish and/or segment data received along the bidirectional communication link, and so on.

The bidirectional communication link may be a wired (e.g., by means of a physical conductor) and/or wireless communication (e.g., utilizing radio frequency (RF)) link for exchanging data (e.g., a data packet) between the one or more alternate ultrasonic imaging systems, remote servers, etc. The bidirectional communication link may be based on a standard communication protocol, such as Ethernet, TCP/IP, WiFi, 802.11, a customized communication protocol, Bluetooth, etc.

The controller circuit 102 is operatively connected to the display device 138 and the user interface 142. The display device 138 may include one or more liquid crystal display devices (e.g., light-emitting diode (LED) backlights), organic light-emitting diode (OLED) display devices, plasma display devices, CRT display devices, and the like. The display device 138 may display patient information, one or more medical images and/or videos, a graphical user interface, or a component received by the display device 138 from the controller circuit 102, one or more 2D, 3D, or 4D ultrasound image data sets from ultrasound data stored in the memory 106, or an anatomical measurement, a diagnosis, processing information, and the like currently acquired in real time.

The user interface 142 controls operations of the controller circuit 102 and the ultrasonic imaging system 100. The user interface 142 is configured to receive an input from a clinician and/or an operator of the ultrasonic imaging system 100. The user interface 142 may include a keyboard, a mouse, a trackball, a touch pad, one or more physical buttons, and the like. Optionally, the display device 138 may be a touch screen display device that includes at least a portion of the user interface 142. For example, a portion of the user interface 142 may correspond to a graphical user interface (GUI) that is generated by the controller circuit 102 and is shown on the display device 138. The touch screen display device may detect the presence of a touch from the operator on the display device 138, and may also identify the position of the touch relative to a surface region of the display device 138. For example, a user may select, by touching or coming into contact with the display device 138, one or more user interface components of the user interface (GUI) shown on the display device. The user interface components may correspond to icons, text boxes, menu bars, etc., shown on the display device 138. A clinician may select, control, and use the user interface components, interact with the same, and so on, so as to send an instruction to the controller circuit 102 to perform one or more operations described in the present application. For example, touch can be applied using at least one among a hand of an individual, a glove, a stylus, and the like.

The memory 106 includes a parameter, an algorithm, one or more ultrasonic examination protocols, data values, and the like used by the controller circuit 102 to perform one or more operations described in the present application. The memory 106 may be a tangible and non-transitory computer-readable medium such as a flash memory, a RAM, a ROM, an EEPROM, etc. The memory 106 may include a set of learning algorithms (e.g., a convolutional neural network algorithm, a deep learning algorithm, a decision tree learning algorithm, etc.) configured to define an image analysis algorithm. During execution of the image analysis algorithm, the controller circuit 102 is configured to identify a section (or a view or an anatomical plane) of an anatomical structure of interest in a medical image. Optionally, the image analysis algorithm may be received by means of the communication circuit 104 along one bidirectional communication link, and stored in the memory 106.

The image analysis algorithm may be defined by one or more algorithms to identify, on the basis of one or more anatomical features within the medical image (e.g., a boundary, thickness, pixel value change, valve, cavity, chamber, edge or inner layer, vessel structure, etc.), a modality or pattern of the medical image (e.g., color blood flow), etc., a section of a subject of interest to be scanned. The one or more anatomical features may represent pixel and/or voxel features of the medical image, such as a histogram of oriented gradients, a point feature, a covariance feature, a binary mode feature, and the like. For example, the image analysis algorithm may be defined by means of prediction of object identification within the medical image by using one or more deep neural networks.

The image analysis algorithm may correspond to an artificial neural network formed by the controller circuit 102 and/or the remote server. The image analysis algorithm may be divided into two or more layers, such as an input layer for receiving an input image, an output layer for outputting an output image, and/or one or more intermediate layers. Layers of a neural network represent different groups or sets of artificial neurons, and may represent different functions that are executed by the controller circuit 102 with respect to the input image (e.g., an ultrasound image acquired and/or generated by the ultrasonic imaging system 100) to identify an object of the input image and determine a section of an anatomical structure of interest shown in the input image. Artificial neurons in a layer of the neural network may examine individual pixels in the input image. The artificial neurons use different weights in a function applied to the input image so as to attempt to identify an object in the input image. The neural network generates an output image by assigning or associating different pixels in the output image with different anatomical features on the basis of the analysis of pixel characteristics.

The image analysis algorithm is defined by a plurality of training images, and the plurality of training images may be grouped into different anatomical planes of interest of the anatomical structure of interest. The training images may represent different orientations and/or cross sections of the anatomical structure of interest corresponding to different fields of view. Additionally or alternatively, the image analysis algorithm may be defined by the controller circuit on the basis of a classification model. The classification model may correspond to a machine learning algorithm based on a classifier (e.g., a random forest classifier, principal component analysis, etc.) which is configured to identify and/or assign anatomical features to multiple types or categories on the basis of overall shape, spatial position relative to the anatomical structure of interest, intensity, etc.

The controller circuit 102 executing the image analysis algorithm (e.g., an image analysis algorithm) may determine, on the basis of the relationship between the anatomical features, modality, etc., a section corresponding to a current ultrasound image.

Additionally or alternatively, the controller circuit 102 may define a separate image analysis algorithm customized and/or configured for different selected anatomical structures of interest. For example, multiple image analysis algorithms may be stored in the memory 106. Each algorithm among the plurality of image analysis algorithms may be customized and/or configured on the basis of different training images (e.g., a set of input images) to configure layers of different neural networks, so as to select anatomical structures of interest, classification models, supervised learning models, and the like.

In some other embodiments, the image analysis algorithm of the controller circuit 102 may also be any other means in the art. For example, the image analysis algorithm may be an algorithm that identifies a boundary of a structure of interest in an image on the basis of changes in an image grayscale value. For example, a certain grayscale value threshold may be set, and neighboring pixel points in the image are compared by using the threshold. If the grayscale value of a neighboring pixel point is greater than the above-described grayscale value threshold, it is determined that said position is a position to be identified, e.g., may be a boundary of a structure of interest. The structure of interest may be a lesion (e.g., a tumor). In addition, it may also be determined that the position is the position at which an interventional object (e.g., a needle) is located, thereby identifying the interventional object. In addition, it should be noted that the example of image identification performed by the controller circuit 102 is described in the foregoing embodiment of the present application, but identification means are not limited thereto, and are not further enumerated herein.

With continued reference to FIG. 1, the ultrasonic imaging system 100 may include a probe 126 and a driving device 108. The driving device 108 is connected to the probe 126 and the controller circuit 102 to receive a control signal of the controller circuit 102 to drive, under the control thereof, the probe 126 to move. The driving device 108 includes an electric motor and an action mechanism connected to the electric motor. In an example, the action mechanism driven by the electric motor can drive the probe to move. Motion forms may include rectilinear motion, rotation, etc., thereby satisfying different scan requirements. In an interventional operation, the driving device 108 drives the probe 126 to move rectilinearly, thereby adjusting the depth of the probe 126 in the body of a person to be imaged. The driving device 108 may also drive the probe 126 to rotate. The combination of rectilinear motion and rotation enables the probe 126 to image, in different directions, a tissue to be imaged, thereby satisfying different scan requirements.

The probe 126 has elements such as an ultrasonic transducer, a transmitter, a transmit beamformer, a detector/SAP electronics, etc., (not shown). The detector/SAP electronics may be used to control the switching of transducer elements. The detector/SAP electronics may also be used to group the transducer elements into one or more sub-holes. Configurations of the probe 126 will also be described below exemplarily.

The probe 126 may be configured to acquire ultrasound data or information from an anatomical structure of interest (e.g., organs, blood vessels, heart, bones, etc.) of a patient. The probe 126 is communicatively connected to the controller circuit by means of the transmitter. The transmitter transmits a signal to the transmit beamformer on the basis of acquisition settings received by the controller circuit 102. The acquisition settings may define the amplitude, pulse width, frequency, gain setting, scanning angle, power, time gain compensation (TGC), resolution, and the like of ultrasonic pulses emitted by the ultrasonic transducer. The ultrasonic transducer emits a pulsed ultrasonic signal into a patient (e.g., the body). The acquisition settings may be defined by a user operating the user interface 142. The signal transmitted by the transmitter, in turn, drives the ultrasonic transducer.

The ultrasonic transducer transmits a pulsed ultrasonic signal to a body (e.g., a patient) or a volume that corresponds to an acquisition setting along one or more scanning planes. The ultrasonic signal may include, for example, one or more reference pulses, one or more push pulses (e.g., shear waves), and/or one or more pulsed wave Doppler pulses. At least a portion of the pulsed ultrasonic signal is backscattered from the tissue to be imaged (e.g., the organ, bone, heart, breast tissue, liver tissue, cardiac tissue, prostate tissue, newborn brain, embryo, abdomen, etc.) to produce an echo. Depending on the depth or movement, the echo is delayed with respect to time and/or frequency, and received by the ultrasonic transducer. The ultrasonic signal may be used for imaging, for producing and/or tracking the shear waves, for measuring changes in position or velocity within the anatomical structure and compressive displacement difference (e.g., strain) of the tissue, and/or for treatment and other applications. For example, the probe 126 may deliver low energy pulses during imaging and tracking, deliver medium and high energy pulses to produce shear waves, and deliver high energy pulses during treatment.

The ultrasonic transducer converts a received echo signal into an electrical signal that can be received by a receiver. The receiver may include one or more amplifiers, analog/digital converters (ADCs), and the like. The receiver may be configured to amplify the received echo signal after suitable gain compensation, and convert the analog signals received from each transducer element into a digitized signal that is temporally uniformly sampled. The digitized signals representing received echoes are temporarily stored in the memory 106. The digitized signals correspond to backscattered waves received by each transducer element at different times. After being digitized, the signal may still retain the amplitude, frequency, and phase information of the backscattered wave.

Optionally, the controller circuit 102 may retrieve a digitized signal stored in the memory 106 for use in a beamformer processor. For example, the controller circuit 102 may convert the digitized signal into a baseband signal or compress the digitized signal.

In some embodiments, the controller circuit 102 may further include a beamformer processor. The beamformer processor may include one or more processors. If desired, the beamformer processor may include a central processing unit (CPU), one or more microprocessors, or any other electronic assembly capable of processing inputted data according to specific logic instructions. Additionally or alternatively, the beamformer processor may execute instructions stored on a tangible and non-transitory computer-readable medium (e.g., the memory 106) to perform beamforming computation by using any suitable beamforming method, such as adaptive beamforming, synthetic emission focusing, aberration correction, synthetic aperture, clutter suppression, and/or adaptive noise control, etc.

In some embodiments, the controller circuit 102 may further include a radio frequency (RF) processor. The beamformer processor performs beamforming on the digitized signal of the transducer elements, and outputs an RF signal. The RF signal is then provided to the RF processor for processing the RF signal. The RF processor may include one or more processors. If desired, the RF processor may include a central processing unit (CPU), one or more microprocessors, or any other electronic assembly capable of processing inputted data according to specific logic instructions. Additionally or alternatively, the RF processor may execute instructions stored on a tangible and non-transitory computer-readable medium (e.g., the memory 106). Optionally, the RF processor may be integrated with and/or be part of the controller circuit 102. For example, operations described as being performed by the RF processor may be configured to be performed by the controller circuit 102.

The RF processor may generate, for a plurality of scanning planes or different scanning modes, different ultrasound image data types and/or modes, e.g., B-mode, color Doppler (e.g., color blood flow, velocity/power/variance), tissue Doppler (velocity), and Doppler energy on the basis of a predetermined setting of a first model. For example, the RF processor may generate tissue Doppler data for multiple scanning planes. The RF processor acquires information (e.g., I/Q, B-mode, color Doppler, tissue Doppler, and Doppler energy information) related to multiple data pieces, and stores data information in the memory 106. The data information may include time stamp and orientation/rotation information.

Optionally, the RF processor may include a composite demodulator (not shown) for demodulating an RF signal to generate an IQ data pair representing an echo signal. The RF or IQ signal data may then be provided directly to the memory 106 so as to be stored (e.g., stored temporarily). As desired, an output of the beamformer processor may be delivered directly to the controller circuit 102.

The controller circuit 102 may be configured to process acquired ultrasound data (e.g., RF signal data or an IQ data pair), and prepare and/or generate an ultrasound image data frame representing the anatomical structure of interest so as to display the same on the display device 138. The acquired ultrasound data may be processed by the controller circuit 102 in real time when an echo signal is received in a scanning or treatment process of ultrasound examination. Additionally or alternatively, the ultrasound data may be temporarily stored in the memory 106 in a scanning process, and processed in a less than real-time manner in live or offline operations.

The memory 106 may be used to store processed frames of acquired ultrasound data that are not scheduled to be immediately displayed, or may be used to store post-processed images (e.g., shear wave images and strain images), firmware or software corresponding to, for example, a graphical user interface, one or more default image display settings, programmed instructions, and the like. The memory 106 may store a medical image, such as a 3D ultrasound image data set of ultrasound data, wherein such a 3D ultrasound image data set is accessed to present 2D and 3D images. For example, a 3D ultrasound image data set may be mapped to the corresponding memory 106 and one or more reference planes. Processing of ultrasound data that includes the ultrasound image data set may be based in part on user input, e.g., a user selection received at the user interface 142.

In some embodiments, the ultrasonic imaging system described above may be configured for use in real-time imaging in an interventional operation. For example, in an interventional operation of the prostate, a doctor may use a probe running through a cavity (e.g., the rectum) to image the prostate and a lesion in the prostate in real time. In addition, a grid plate may also be used for guiding of an interventional position of the interventional object. The grid plate includes a plurality of interventional holes. Position coordinates of the interventional holes may correspond to coordinates on an ultrasound image. An operator can determine, by observing a structure of interest in the ultrasound image, a coordinate point set on which an interventional operation needs to be performed, and then find a corresponding coordinate point set from upon the grid plate to perform a next operation. Switching the line of sight between the ultrasound image and the grid plate causes the entire operation process to be time consuming and laborious, and increases pain of a patient. At least in view of this, the ultrasonic imaging system 100 of the present application may further include the grid assembly 201. As shown in FIG. 1, the grid assembly 201 communicates with the controller circuit 102 (e.g., a processor in the controller circuit 102). Such configurations can enable the controller circuit 102 to act on the grid assembly 201, and/or enable the grid assembly 201 to provide feedback to the controller circuit 102. A detailed description of a control means and a feedback means will be provided below in the present application.

Referring to FIG. 2, FIG. 2 shows a schematic diagram of an ultrasonic imaging method 200 in an interventional procedure according to some embodiments of the present application. The interventional procedure may be performed on a structure of interest by using the grid assembly 201 to guide an interventional object. The method 200 can be implemented by the ultrasonic imaging system disclosed in any embodiment herein.

In step 201, a coordinate point set of a position to be subjected to intervention on an ultrasound image of a structure of interest is acquired. The process may be implemented by the processor. In one example, the above-described structure of interest may be a lesion to be subjected to intervention, e.g., a prostate tumor. The position to be subjected to intervention may be determined by any means in the art, and is a position at which an interventional operation needs to be performed on the structure of interest. For example, the position to be subjected to intervention may be a position that is determined in the prostate tumor by an operator by performing determination and planning in advance. In one example, the operator may perform ultrasonic imaging on the structure of interest in advance, comprehensively determine an overall contour of the structure of interest, and then determine, according to the overall contour, a representative position to be subjected to intervention (an exemplary description will be provided below). The representative interventional position may be selected according to an actual factor. For example, comprehensive consideration may be performed according to the size of the structure of interest, representativeness of sampling of the interventional operation, or the action range of administration. After consideration, the above-described coordinate point set of the position to be subjected to intervention may be a set of selected coordinate points within a range covered by the overall contour of the structure of interest. In another example, the means of the above-described determination may be automatic. For example, a point that needs to be subjected to intervention is automatically determined by means of the ultrasonic imaging system according to an identification result of an outer contour of the structure of interest. It should be noted that the above description is merely an exemplary description of the determination means of the coordinate point position of the position to be subjected to intervention. These determinations of the coordinate point set mainly serve as a precondition for acquiring the coordinate point set in step 201 of the present application. The present application is not intended to impose any limitations on such a determination means, and the determination means of the coordinate point set may also be any other means. After the coordinate point set is determined, the above-described determination result may be acquired by the processor. In one example, an acquisition means may be the operator using the user interface 142 to perform an operation on an ultrasound image displayed on the display device 138, thereby enabling the processor to acquire the same. In another example, the acquisition means may be performed automatically by the ultrasonic imaging system. For example, the ultrasonic imaging system performs automatic identification first to acquire the coordinate point set of the position to be subjected to intervention, and does not require additional input.

In step 202, a display unit on the grid assembly is controlled on the basis of the coordinate point set to cause the display unit to generate a first visual indication for an interventional hole which is on the grid assembly and which falls within the coordinate point set. The process may be implemented by the processor. As described above in the present application, in a conventional interventional operation, an ultrasound image of an outer contour of a structure of interest which itself is provided with coordinates is displayed. The coordinates on the ultrasound image are adjusted in advance to match coordinates of each interventional hole on the grid plate, so that the operator can find a corresponding interventional hole on the grid plate according to the coordinates on the ultrasound image to perform an operation. In step 202 of the present application, the processor can control, on the basis of the coordinate point set of the ultrasound image acquired in step 201, the display unit on the grid assembly to perform display. Specifically, the processor controls the display unit to cause an interventional hole which is on the grid assembly and which falls within the above-described coordinate point set to generate the first visual indication. For example, the display unit may cause the position of one or more interventional holes which fall within the coordinate point set to emit light.

In this way, when the operator needs to perform an operation, the operator no longer needs to switch the line of sight thereof between the ultrasound image and the grid, and only needs to observe visual guidance of the display unit on the grid plate in order to quickly and accurately determine the position of a target interventional hole, which can greatly increase the efficiency of the operator.

It can be understood that given the above-described teaching of the present application, configurations of the display unit of the grid assembly may be diverse. In one aspect, the display unit can selectively perform display under the control of the controller circuit of the ultrasonic imaging system, and in another aspect, can correspond to the interventional hole on the grid assembly. An exemplary description is provided in the following embodiments herein.

Figure 3:
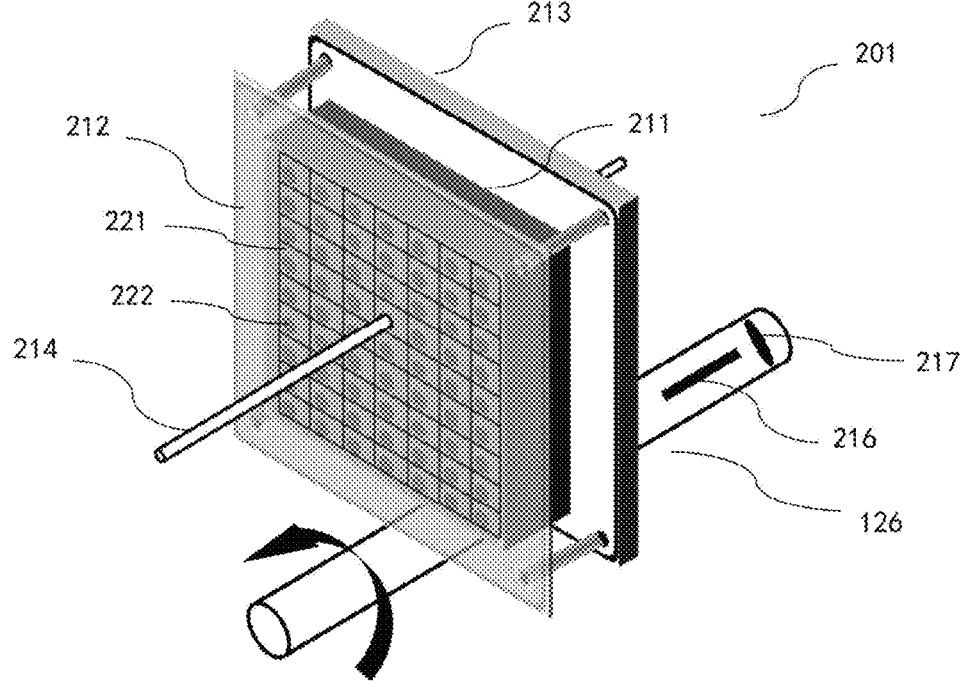
FIG. 3 is a schematic diagram of a grid assembly according to some embodiments of the present application.

Reference is initially made to FIG. 3, and FIG. 3 is a schematic diagram of the grid assembly 201 according to some embodiments of the present application.

As shown in FIG. 3, the grid assembly 201 may include a grid plate 211 and a display unit 212. The grid plate includes interventional holes 222, and each interventional hole corresponds to a coordinate point on the ultrasound image (not shown in FIG. 3). The display unit 212 can generate a visual indication for each interventional hole 222.

In one example, the display unit 212 may be, as shown in FIG. 3, a display plate covering an external side of the grid plate 211. For example, the display plate may include a plurality of lights 221, and each light 221 can correspond to each interventional hole 222. In this way, when visual indication needs to be performed for any number of interventional holes 222, a light-emitting state of the corresponding lights 221 may be controlled. For example, the interventional hole 222 corresponding to a light that is emitting light may be used to represent the interventional hole which falls within the coordinate point set. Moreover, in another embodiment, changes in the light-emitting state of each light 221 may also include a change in color. Operation progress of the corresponding interventional hole may be indicated by the change in color. For example, an interventional hole that has been subjected to an interventional operation may be indicated by using a color, and an interventional hole that has not been subjected to an interventional operation may be indicated by using another color. It can be understood that in order not to hinder an operator from using the grid plate to guide an interventional object, the display unit 212 may likewise include a plurality of holes. Furthermore, in another embodiment, the display unit 212 and the grid plate 211 may be integrally arranged. That is, the lights 221 may be directly provided on the grid plate 211 to emit light to perform display. Enumeration is not further provided. The ultrasonic imaging method described above in the present application can be implemented by means of a mating relationship between the display unit 212 and the grid plate 211, which can increase the operating efficiency and improve the accuracy of the operator.

In another example, the grid assembly 201 may further include an interventional object sensing unit 213. The interventional object sensing unit 213 can sense an interventional object 214 penetrating an interventional hole 222 to generate a sensing signal. The interventional object sensing unit 213 may be arranged corresponding to the grid plate 211. In this way, when the interventional object 214 penetrates the interventional object sensing unit 213, since the interventional object sensing unit 213 and the grid plate 211 are correspondingly arranged, at said time, coordinate information of the interventional object 214 sensed by the interventional object sensing unit 213 corresponds to coordinate information on the grid plate 211 through which the interventional object 214 penetrates. In some embodiments, the interventional object sensing unit 213 may be, as shown in FIG. 3, arranged separately from the grid plate 211. In some other examples, the interventional object sensing unit 213 and the grid plate 211 may likewise be integrally arranged. For example, in some examples, the grid plate 211, the display unit 212, and the interventional object sensing unit 213 that are integrally arranged collectively form the grid assembly 201.

With continued reference to FIG. 3, the probe 126 may mate with the grid assembly 201. In one example, the probe 126 includes a stem-shaped portion, and an ultrasonic transducer 216 extends in the length direction of the stem-shaped portion. It can be understood that a plane imaged by the ultrasonic transducer 216 is parallel to a plane in which the interventional object 214 is located. Furthermore, driven by the driving device, the probe 126 can move (e.g., rotation indicated by an arrow in FIG. 3), so that the imaging plane of the ultrasonic transducer 216 passes through the interventional object, and the interventional object is imaged according to the means described in any embodiment of the present application. In addition, the probe 126 may further include an ultrasonic transducer 217. The ultrasonic transducer 217 may be perpendicular to the ultrasonic transducer 217, and is configured to image a structure of interest, e.g., is configured to image the planned interventional position described above. Details will not be described again.

Configurations of the interventional object sensing unit may be diverse. In general, the interventional object includes a metal material. Correspondingly, the interventional object sensing unit 213 may be a sensor capable of sensing a metal. For example, the sensor may include a magnetic sensor, an electric sensor, or any type of sensor. The present application does not impose any exclusive limitations on specific configurations of the interventional object sensing unit. An exemplary description of only preferred embodiments thereof is provided below.

Figure 4:
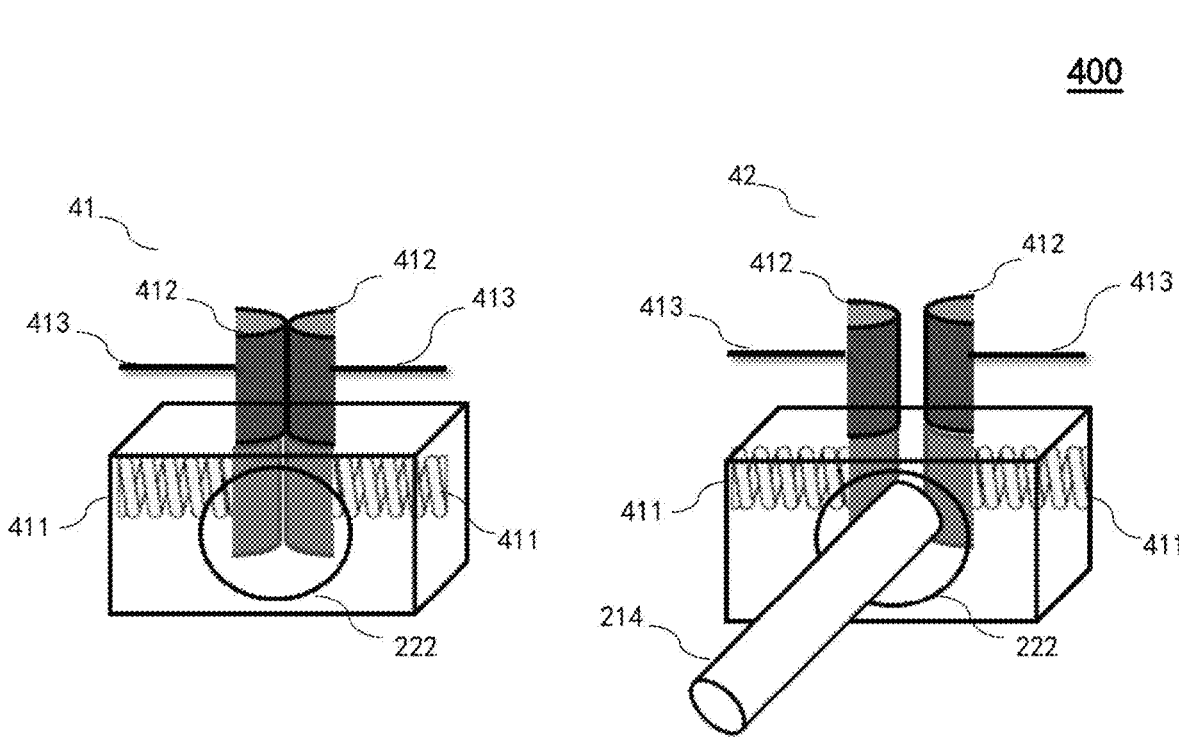
FIG. 4 is a schematic diagram of an interventional object sensing unit sensing an interventional object according to some embodiments of the present application.

Referring to FIG. 4, FIG. 4 is a schematic diagram 400 of an interventional object sensing unit sensing an interventional object according to some embodiments of the present application. A portion of the interventional object sensing unit (the entirety is not shown) corresponding to any number of interventional holes 222 may include a sensor 401. The sensor 401 may include an elastic element 411, sensing elements 412, and wires 413. The elastic element 411 is elastically connected to the sensing elements 412. The sensing elements 412 are connected to the wires 413.

Reference is initially made to FIG. 41. When the interventional object 214 is not inserted, two sensing elements 412 are attached together under the action of the elastic element 411. At said time, conductive structures of end portions of the sensing elements 412 conduct due to contact therebetween. Correspondingly, the wires 413 to which the two sensing elements 412 are respectively connected are also in a conducting state. In this way, when the two wires 413 are connected to an external circuit (not shown), the circuit is in a connected state. An electrical feature (e.g., any one or a plurality of the voltage, the current, the resistance, the capacitance, and the like) of the circuit at this time point is recorded. Referring to FIG. 42, when the interventional object 214 is inserted, the two sensing elements 412 are separated due to the insertion of the interventional object. At said time, to-point structures of the end portions of the sensing elements 412 are disconnected due to separation. Correspondingly, the wires 413 to which the two sensing elements 412 are respectively connected are also in a short-circuited state. At said time, the electrical feature (e.g., any one or a plurality of the voltage, the current, the resistance, and the capacitance) of the external circuit changes due to the insertion of the interventional object 214. By means of recording the change, the specific position of the interventional object sensing unit through which the interventional object 214 penetrates can be sensed. Furthermore, as described above, the position of the interventional object sensing unit corresponds to the grid plate 212. Correspondingly, the coordinates of the grid plate 212 through which the interventional object 214 penetrates can be sensed.

It should be noted that the above-described configurations of the interventional object sensing unit are merely a preferred example of the present application, and no exclusive definition is made.

The inventor is aware that integrating the interventional object sensing unit into the grid assembly can more advantageously increase the operating efficiency of the operator. An exemplary description is provided below.

Figure 5:
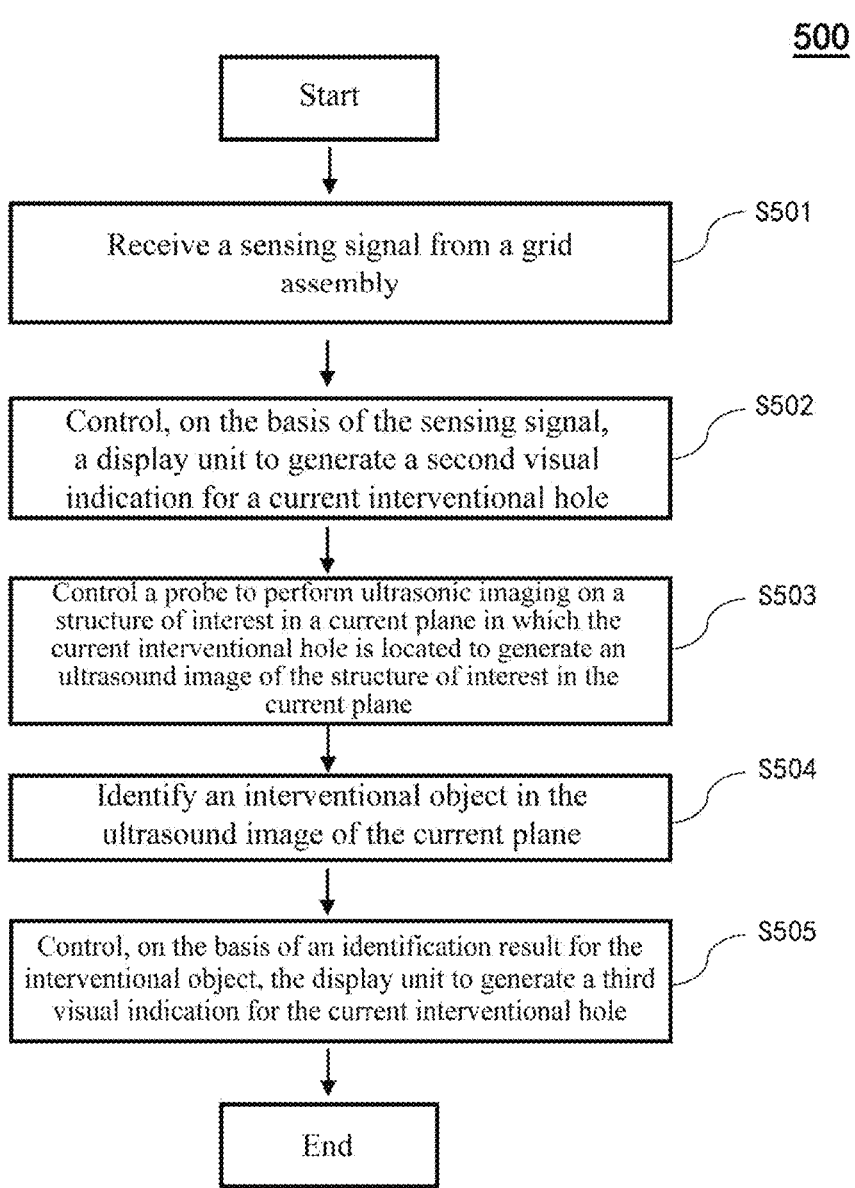
FIG. 5 is a schematic diagram of an ultrasonic imaging method according to some other embodiments of the present application.

Referring to FIG. 5, FIG. 5 shows a schematic diagram of an ultrasonic imaging method 500 according to some other embodiments of the present application. The method 500 can be implemented by the ultrasonic imaging system disclosed in any embodiment herein.

In step 501, a sensing signal is received from the grid assembly, the sensing signal being generated by the grid assembly on the basis of the interventional object penetrating a current interventional hole. The process may be implemented by the processor of the ultrasonic imaging system. In one example, the above-described sensing signal may be generated by a detection result of the interventional object sensing unit 213 included in the grid assembly 201. An exemplary description is provided above, and details will not be described again.

In step 502, the display unit is controlled on the basis of the sensing signal to generate a second visual indication for the current interventional hole. The process may be implemented by the processor. Specifically, as described above, the sensing signal includes coordinate information of the interventional hole through which the current interventional object passes. The processor may specifically control the display unit on the grid assembly to perform, for the current interventional hole, the second visual indication that is different from the first visual indication described above. In one example, the first and second visual indications may be different in color. In another example, the first and second visual indications may be different in terms of other display means, e.g., different frequencies of blinking, different durations for which lights are on, etc. Enumeration is not further provided.

In such a configuration, not only it is possible to highlight, by means of the ultrasonic imaging system, an interventional hole in the grid assembly that needs to be subjected to an interventional operation, but also, another type of visual indication can be performed on an interventional hole being (or that has been) subjected to an interventional operation, so that the effect of prompting an operator can be further improved, thereby increasing the operating efficiency.

In step 503, a probe is controlled to perform ultrasonic imaging on the structure of interest in a current plane in which the current interventional hole is located to generate an ultrasound image of the structure of interest in the current plane. The process may be implemented by the processor. The above-described driving process may be implemented by the driving device described above. In one example, first, the operator may operate the probe to move the same. For example, the operator rotates the probe until an ultrasonic signal transmitted by the ultrasonic transducer on the probe passes through the plane in which the current interventional hole is located, so that ultrasonic imaging can be performed on the structure of interest of the current plane. In another example, the above-described process may be automatically controlled and implemented by the processor, thereby further increasing efficiency. Specifically, the processor may determine, on the basis of the sensing signal, position information of the current interventional hole, and further control, on the basis of the position information, the driving device to drive the probe to move. As described above, upon receiving the sensing signal from the grid assembly, the processor can determine which interventional hole the sensing signal is specifically from. That is, the position information of the interventional hole is determined by the processor. In this case, the processor can derive, by means of calculation, an angle of rotation that is required to control the probe to move from a current position (e.g., a default initial position or a position that was adjusted by a previous interventional operation) to a position corresponding to the current interventional hole. The specific calculation means may be any means in the art, and details will not be described again. Such a configuration can better improve automation of the ultrasonic imaging procedure, thereby reducing the degree of complexity of a workflow of the operator.

In step 504, the interventional object is identified in the ultrasound image of the current plane. The process may be implemented by the processor. The specific identification means may be the means described in any embodiment of the present application described above or another means in the art, and enumeration is not further provided.

In step 505, the display unit is controlled, on the basis of an identification result for the interventional object, to generate a third visual indication for the current interventional hole. The process may be implemented by the processor. Such a configuration enables the operator to learn, by observing only the interventional hole and the display unit, whether an operation in the current interventional position is in place, and manual determination after observing the ultrasound image of the ultrasonic imaging system is not needed. An exemplary description of the type of the third visual indication is provided below.

In some examples, the processor may determine, according to the identification result for the interventional object, whether the position of the interventional object in the ultrasound image is correct. For example, if the position of the interventional object has reached the desired ultrasonic imaging system position, the display unit may be controlled to use the third visual indication to indicate the current interventional hole. Such a configuration enables the operator, while focusing on the interventional operation, to determine, by observing only the grid assembly, whether the interventional operation is in place, thereby greatly simplifying a workflow.

In some other examples, the processor may determine, according to the identification result for the interventional object, whether the interventional object appears in the ultrasound image and then disappears. If so, it can be determined that the interventional operation at the coordinates of the current interventional hole has been completed. In this case, the display unit is controlled to use the third visual indication to indicate the current interventional hole, which can enable the operator to be able to determine, by observing only the grid assembly, whether intervention of the current hole has been completed. Especially when the coordinate set corresponds to too many interventional holes, such a configuration can enhance the confidence of the operator.

By means of the embodiments described above, throughout the workflow of the operator, the problem in which the operator needs to simultaneously observe the ultrasound image and the grid assembly during the ultrasonic imaging procedure and the interventional procedure can be minimized to the greatest degree. For example, the operator may pay more attention to the grid assembly, and complete the operation by means of visual guidance provided by the display unit on the grid assembly.

It will be appreciated that the foregoing merely schematically illustrates the embodiments of the present application, but the present application is not limited thereto. For example, the order of execution between operations may be suitably adjusted. In addition, some other operations may be added or some operations may be omitted. For example, any number of steps among all of the steps recited in the above embodiments of the present application may be performed, or these steps may be reasonably combined. A person skilled in the art could make suitable variations according to the above disclosure rather than being limited by the above descriptions.

The principle of the present application is described more clearly below by means of graphic representation. Referring to FIG. 6, FIG. 6 shows a schematic diagram 600 of an ultrasonic imaging system controlling a grid assembly according to some embodiments of the present application. An ultrasound image 601 may be an image for a structure of interest 611, and may be obtained by means of imaging performed by the ultrasonic transducer 217 as shown in FIG. 3. The ultrasound image of the structure of interest 611 includes a plurality of coordinate point sets 612. Correspondingly, these sets 612 are visually displayed on the grid assembly 201. Interventional holes 613 on the grid assembly 201 corresponding to the coordinate point sets 612 are highlighted. The specific highlighting means are described above in detail, and details will not be described again. In addition, a display means of these highlighted interventional holes 613 may also vary according to the status of an operation to be performed. For example, the first visual indication (e.g., a first color) is displayed in an initial state, and the second visual indication (e.g., a second color) is displayed when the interventional object penetrates a certain interventional hole. In addition, the third visual indication may also be generated according to the identification result for the interventional object in the ultrasound image (e.g., an image acquired by the ultrasonic transducer 216). For example, a color is displayed when the interventional object reaches a predetermined position, and another color is displayed when the interventional object disappears from the image, and so on. In addition, once one interventional hole operation is completed, the ultrasonic imaging system may further be configured to automatically determine an interventional hole corresponding to a next intervention, and generate a fourth visual indication (e.g., a fourth color) for the same. An automatic determination means may be, in the above-described interventional hole, the ultrasonic imaging system performing automatic path planning and selecting an optimal path, thereby saving as much time as possible and increasing efficiency.

Some embodiments of the present application further provide an ultrasonic imaging system, which may be as shown in FIG. 1 or any other ultrasonic imaging system. The system includes: a probe, including an ultrasonic transducer; a processor, configured to perform the method according to any embodiment described herein; a display device, configured to receive a signal from the processor so as to perform display; and a grid assembly, communicating with the processor.

Some embodiments of the present application further provide a non-transitory computer-readable medium, having a computer program stored therein, the computer program having at least one code segment, and the at least one code segment being executable by a machine so as to enable the machine to perform the steps of the method in any of the embodiments described above.

Correspondingly, the present disclosure may be implemented as hardware, software, or a combination of hardware and software. The present disclosure may be implemented in at least one computer system by using a centralized means or in a distributed means, different elements in the distributed means being distributed on a number of interconnected computer systems. Any type of computer system or other device suitable for implementing the methods described herein is considered to be appropriate.

The various embodiments may also be embedded in a computer program product, which includes all features capable of implementing the methods described herein, and the computer program product is capable of executing these methods when loaded into a computer system. The computer program in this context means any expression in any language, code, or symbol of an instruction set intended to enable a system having information processing capabilities to execute a specific function directly or after any or both of a) conversion into another language, code, or symbol; and b) duplication in a different material form.

The purpose of providing the above specific embodiments is to facilitate understanding of the content disclosed in the present invention more thoroughly and comprehensively, but the present invention is not limited to these specific embodiments. Those skilled in the art should understand that various modifications, equivalent replacements, and changes can also be made to the present invention and should be included in the scope of protection of the present invention as long as these changes do not depart from the spirit of the present invention.

What is claimed is:

1. An ultrasonic imaging method in an interventional procedure, the interventional procedure being performed on a structure of interest by using a grid assembly to guide an interventional object, the method comprising:

acquiring a coordinate point set of a position to be subjected to intervention on an ultrasound image of the structure of interest;

controlling, based on the coordinate point set, a display unit on the grid assembly to cause the display unit to generate a first visual indication for an interventional hole which is on the grid assembly and which falls within the coordinate point set; and automatically control, based on the interventional object being inserted into a current interventional hole of the grid, a transducer of a probe to align a current plane of the probe with the current interventional hole and the structure of interest.

2. The ultrasonic imaging method according to claim 1, further comprising:

receiving a sensing signal from the grid assembly, the sensing signal being generated by the grid assembly based on the interventional object penetrating the current interventional hole; and controlling, based on the sensing signal, the display unit to generate a second visual indication for the current interventional hole.

3. The ultrasonic imaging method according to claim 2, further comprising:

controlling the probe to perform ultrasonic imaging on the structure of interest in the current plane in which the current interventional hole is located to generate an ultrasound image of the structure of interest in the current plane.

4. The ultrasonic imaging method according to claim 3, further comprising:

identifying the interventional object in the ultrasound image of the current plane; and controlling, based on an identification result for the interventional object, the display unit to generate a third visual indication for the current interventional hole.

5. The ultrasonic imaging method according to claim 3, wherein the controlling of the probe comprises:

determining, based on the sensing signal, position information of the current interventional hole; and controlling, based on the position information, a driving device to drive the transducer of the probe to move.

6. The ultrasonic imaging method according to claim 3, further comprising:

automatically determining an interventional hole corresponding to a next intervention, and generating a fourth visual indication for the interventional hole corresponding to the next intervention.

7. An ultrasonic imaging system, comprising:

a probe, comprising an ultrasonic transducer;

a processor, configured to perform the method according to claim 1;

a display device, configured to receive a signal from the processor to perform display; and a grid assembly, communicating with the processor.

8. The ultrasonic imaging system according to claim 7, wherein the grid assembly comprises:

a grid plate, comprising interventional holes, the interventional holes corresponding to coordinate points on an ultrasound image;

an interventional object sensing unit, the interventional object sensing unit sensing an interventional object penetrating an interventional hole to generate a sensing signal; and a display unit, the display unit generating visual indications for the interventional holes.

9. The system according to claim 7, wherein the probe comprises a stem-shaped portion, and the ultrasonic transducer extends in the length direction of the stem-shaped portion.

10. The system according to claim 7, further comprising:

a driving device, connected to the probe and configured to drive the probe to move.

11. A non-transitory computer-readable medium, having a computer program stored therein, the computer program having at least one code segment, and the at least one code segment being executable by a machine to cause the machine to perform steps of the method according to claim 1.

12. The method of claim 1, wherein automatically controlling the transducer comprises rotating the probe about its longitudinal axis to align the imaging plane with the current interventional hole.

13. The method of claim 1, wherein automatically controlling the transducer further comprises adjusting a depth of the probe by linear translation to position the imaging plane through the structure of interest.

14. The method of claim 1, wherein automatically controlling the transducer comprises calculating an angle of rotation required to align the imaging plane with the current interventional hole based on position information of the hole.

\* \* \* \* \*